(12) United States Patent
Kim et al.

(10) Patent No.: US 10,308,973 B1
(45) Date of Patent: Jun. 4, 2019

(54) REAL-TIME IMAGING METHOD OF NAPDH-DEPENDENT METABOLIC ACTIVITY IN CELL AND USE THEREOF

(71) Applicant: INDUSTRY FOUNDATION OF CHONNAM NATIONAL UNIVERSITY, Gwangju (KR)

(72) Inventors: Geun-Joong Kim, Gwangju (KR); Eung Sam Kim, Gwangju (KR); Jeong Sun Kim, Gwangju (KR); Sung Hwan You, Gwangju (KR); Dae Eun Cheong, Gwangju (KR); Eun Seo Jo, Gwangju (KR)

(73) Assignee: Industry Foundation of Chonnam National University, Gwangju (KR)

( * ) Notice: Subject to any disclaimer, the term of this patent is extended or adjusted under 35 U.S.C. 154(b) by 0 days.

(21) Appl. No.: 16/131,951

(22) Filed: Sep. 14, 2018

(30) Foreign Application Priority Data

Jul. 20, 2018 (KR) ......................... 10-2018-0084490

(51) Int. Cl.
| | |
|---|---|
| C07K 1/00 | (2006.01) |
| C12Q 1/32 | (2006.01) |
| C12N 15/66 | (2006.01) |
| G01N 21/64 | (2006.01) |
| C12N 15/52 | (2006.01) |
| C12N 15/70 | (2006.01) |

(52) U.S. Cl.
CPC ............... *C12Q 1/32* (2013.01); *C12N 15/52* (2013.01); *C12N 15/66* (2013.01); *C12N 15/70* (2013.01); *G01N 21/6428* (2013.01); *C12Y 101/01001* (2013.01)

(58) Field of Classification Search
CPC ...................................................... C12Q 1/32
See application file for complete search history.

(56) References Cited

FOREIGN PATENT DOCUMENTS

| KR | 100950064 B1 | 3/2010 |
|---|---|---|
| KR | 101234583 B1 | 2/2013 |
| KR | 101769789 B1 | 8/2017 |

*Primary Examiner* — Albert M Navarro
(74) *Attorney, Agent, or Firm* — McCoy Russell LLP

(57) ABSTRACT

Provided is a real-time imaging method of NAPDH-dependent metabolic activity in a cell and a use thereof, and more particularly, an imaging method capable of measuring concentration gradient and change in an intracellular coenzyme using a mutant of metagenome-derived blue fluorescent protein (mBFP) in real-time and an application method thereof. In particular, the method of imaging and quantifying the coenzyme contained in various biological samples may be performed by improving fluorescence in a short time even under anaerobic conditions, without adding a substrate required for coenzyme measurement or conversion without destroying cells, and without consuming the time required for formation of a special structure (fluorophore) for generating fluorescence unlike the existing quantitative systems. In particular, provided is a stable quantitative/imaging technique that is directly applicable to biological samples having various complex compositions without signal interference caused by impurities by removing an inherent enzymatic activity of mBFP.

12 Claims, 10 Drawing Sheets

Specification includes a Sequence Listing.

A.

B.

1: E.coli
2: C.glutamicum

1: Hela cell
2: callus

REAL-TIME IMAGING METHOD OF NAPDH-DEPENDENT METABOLIC ACTIVITY IN CELL AND USE THEREOF

CROSS-REFERENCE TO RELATED APPLICATIONS

This application claims priority under 35 U.S.C. § 119 to Korean Patent Application No. 10-2018-0084490, filed on Jul. 20, 2018, in the Korean Intellectual Property Office, the disclosure of which is incorporated herein by reference in its entirety.

STATEMENT REGARDING SEQUENCE LISTING

The sequence listing associated with this application is provided in text format in lieu of a paper copy and is hereby incorporated by reference into the specification. The name of the text file containing the sequence listing is Sequence_Listing_PLS18315.txt. The text file is 14 KB; was created on Sep. 14, 2018; and was submitted via EFS-Web with the filing of the specification on Sep. 14, 2018.

TECHNICAL FIELD

The following disclosure relates to a real-time imaging method of NAPDH-dependent metabolic activity in a cell and a use thereof, and more particularly, to an imaging method capable of measuring concentration gradient and change in an intracellular coenzyme using a metagenome-derived blue fluorescent protein (mBFP) in real-time and an application method thereof.

BACKGROUND

In general, cellular metabolism consists of the production of major precursors and energy by oxidative and catabolic reactions of nutrients input from the outside, and synthesis of biomolecules using the major precursors and energy. The constituents of the bioenergy generated in this process and consumed in the synthesis process are electrons and protons, and coenzymes, NADP(H) and NAD(H), act as the main carrier.

NADP(H) and NAD(H) are essential elements in vivo, and oxidized forms (NAD+ and NADP+) are regenerated (NADH and NADPH) in the central pathway. The ratio between the oxidation and reduction form is also controlled through a regenerative pathway (salvage pathway) that is able to be interconverted between oxidation/reduction forms.

The oxidation/reduction ratio of the coenzymes in cells can be used as an important indicator of bioactivity. The quantification of NADP(H) and NAD(H) may be used to determine whether normal physiology in vivo is maintained, metabolism abnormality occurs, and the like. This may be an important indicator for determining the presence of cells, cell viability, and food contamination in samples, and may be widely applied to other fields as well.

In order to utilize quantitative determination of the coenzymes, various coenzyme measurement methods are being developed. As a representative method, there is a method of measuring absorbance or fluorescence using intrinsic wavelength of NADP(H) or NAD(H), but since the absorbance and the fluorescence value of the coenzymes are quite low, there is a disadvantage in that a relatively accurate measurement value is obtainable only in a defined (artificial) reaction composition, and thus it is difficult to apply this method directly to various kinds of natural samples.

Other methods for quantitative determination of coenzymes are also established. However, it is difficult to separately measure NADP+/NADPH and NAD+/NADH, which are oxidation/reduction forms of coenzyme, and it is difficult to perform the measurement effectively when a concentration of coenzyme is very low. For example, NADP(H) and NAD(H) have similar absorbance and fluorescence spectrums, and thus it is difficult to distinguish the NADP(H) and NAD(H). When an amount of the sample is small, the signal to noise ratio (S/N ratio) is low, and thus it is very difficult to distinguish the NADP(H) and NAD(H). In addition, since oxidized NADP+ has relatively poor optical properties, it is not easy to measure the coenzyme having the corresponding form.

In order to overcome problems known in the related art, a method of using high performance liquid chromatography (HPLC), a method of using a coupling reaction including dehydrogenase which induces coenzyme reduction through oxidation of a specific substrate, or a method of using an artificial fluorescent substance, or the like, has been developed. However, these methods require a multi-step pretreatment protocol, and these methods are not able to be used for direct real-time observation of the coenzyme concentration gradient in the body or for quantitative analysis.

In order to solve the above-described disadvantages, a method using molecular imaging equipment has been developed. A confocal laser scanning microscope is used to observe an intrinsic fluorescence wavelength of the coenzyme with high resolution with a high power continuous wave (CW) laser. Alternatively, two photon microscopy using two photons minimizes cell damage or photobleaching according to single radiation of a high energy wavelength due to two successive radiations with low energy level in an image acquisition process, and thus the measurement of the coenzyme is improved. However, the above method is still a fluorescent measurement method using the intrinsic wavelength of NADPH, and it is difficult to perform accurate quantitative analysis or distinguish NADPH from NADH because the S/N ratio is low, and thus another solution is urgently required.

SUMMARY

An embodiment of the present disclosure is directed to providing a continuous imaging measurement method capable of imaging and quantifying a small amount of the coenzymes in a cell with high sensitivity and efficiency, performing the measurement in seconds, thereby conducting real-time analysis, and causing less stress on cell growth and physiology.

In one general aspect, there is provided a mutant of a blue fluorescent protein mBFP (metagenome-derived blue fluorescent protein) consisting of an amino acid sequence of SEQ ID NO: 1 or SEQ ID NO: 2.

In another general aspect, there is provided a nucleic acid sequence encoding the amino acid sequence of the mutant as described above.

In still another general aspect, there is provided a recombinant expression vector including the nucleic acid sequence as described above.

In another general aspect, there is provided a transformant, excluding human, transformed with the recombinant expression vector as described above.

In another general aspect, there is provided a composition for real-time quantification of NADP(H) in vivo including: a mutant of a blue fluorescent protein mBFP (metagenome-derived blue fluorescent protein) consisting of an amino acid sequence of SEQ ID NO: 1 or SEQ ID NO: 2.

In still another general aspect, there is provided a method for real-time quantification of NADP(H) including: adding a mutant of a blue fluorescent protein mBFP (metagenome-derived blue fluorescent protein) consisting of an amino acid sequence of SEQ ID NO: 1 or SEQ ID NO: 2 to a NADP(H)-dependent oxidase/reductase, and measuring a fluorescence change.

In still another general aspect, there is provided a method for quantifying a NADP(H)-dependent oxidase/reductase including: adding a mutant of a blue fluorescent protein mBFP (metagenome-derived blue fluorescent protein) consisting of an amino acid sequence of SEQ ID NO: 1 or SEQ ID NO: 2 to a NADP(H)-dependent oxidase/reductase, and measuring a fluorescence change.

In another general aspect, there is provided a kit for real-time quantification of NADP(H) including: a mutant of a blue fluorescent protein mBFP (metagenome-derived blue fluorescent protein) consisting of an amino acid sequence of SEQ ID NO: 1 or SEQ ID NO: 2.

DETAILED DESCRIPTION OF EMBODIMENTS

Figure 1:
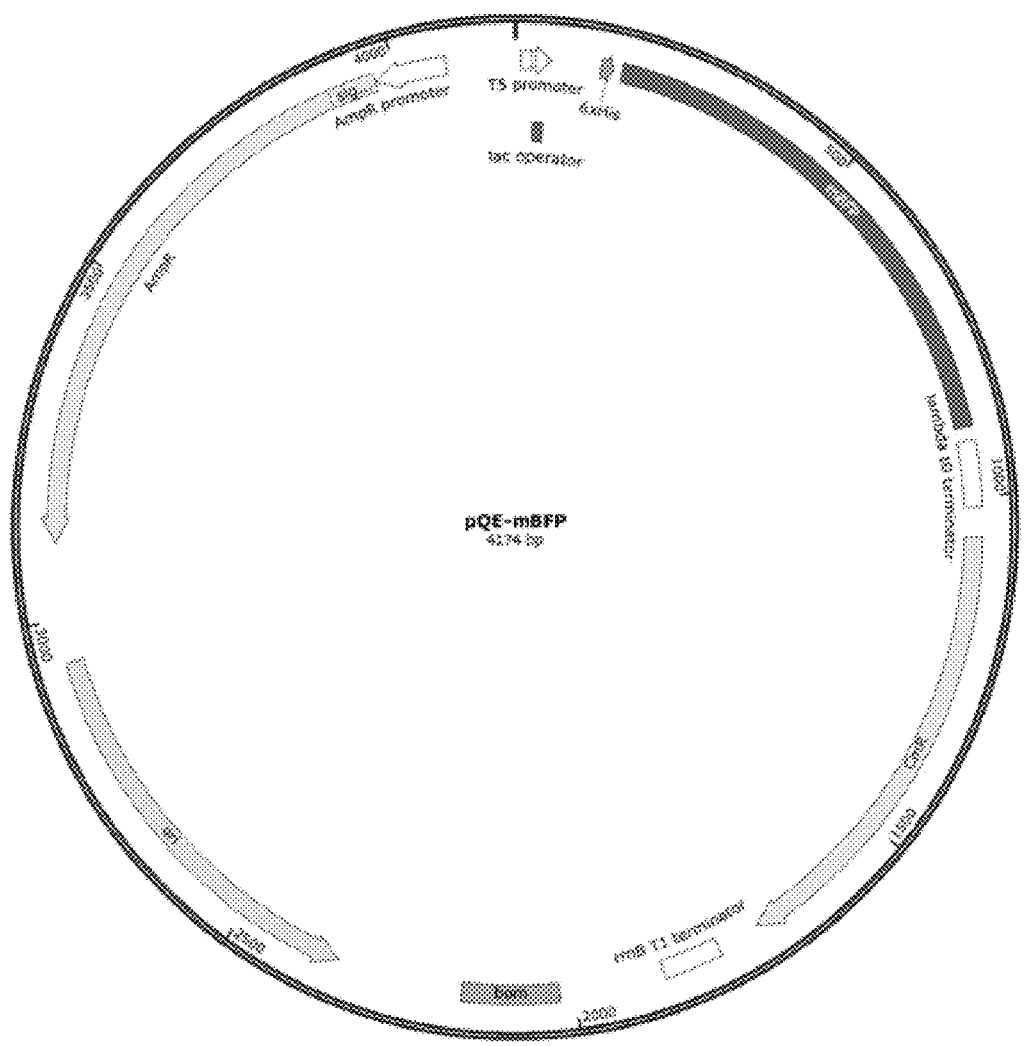
FIG. 1 is a diagram of a vector for expressing the blue fluorescent protein mBFP according to the present disclosure.

Hereinafter, a real-time imaging method of NAPDH-dependent metabolic activity in a cell and a use thereof are described in detail with reference to the accompanying Tables or drawings.

The exemplary embodiments of the present disclosure shown in the drawings are provided by way of example so that the idea of the present disclosure can be sufficiently transferred to those skilled in the art to which the present disclosure pertains. Therefore, the present disclosure may be implemented in many different forms, without being limited to the drawings to be shown below. The drawings may be exaggerated in order to specify the spirit of the present disclosure.

Herein, unless technical and scientific terms are defined otherwise, they have meanings generally understood by those skilled in the art to which the present disclosure pertains. Known functions and components which may obscure the description and the accompanying drawings of the present disclosure with unnecessary detail will be omitted.

"Specimen" or "sample" as used herein refers to an object for analysis and is used with the same meaning throughout the specification.

The term "real-time" as used herein may mean that additional preprocessing or a predetermined waiting time is not included at the time of performing analysis, but is not limited thereto. More specifically, "real-time" may mean that the analysis may be performed within 0.01 to 100 seconds, preferably 0.1 to 60 seconds, more preferably 0.5 to 30 seconds, and more preferably 1 to 15 seconds, but is not limited thereto.

Hereinafter, the present disclosure is described in detail.

The present disclosure provides a mutant of a blue fluorescent protein metagenome-derived blue fluorescent protein (mBFP) consisting of an amino acid sequence of SEQ ID NO: 1 or SEQ ID NO: 2.

The mBFP mutant according to an embodiment of the present disclosure may include an affinity tag, and the affinity tag may use a His-tag. In addition, the mBFP mutant according to an embodiment of the present disclosure may be selected from a protein library expressed using a mutagenesis host that further induces a random mutation in a specific gene so as to remove an activity with respect to specific oxidase/reductase of mBFP, but exhibits the same level of affinity to coenzyme NADPH as that of wild type mBFP; scarcely interferes with mutually competitive optical properties with other coenzymes such as NAD+ and NADH; may minimize quantitative error even when an amount of the desired coenzyme is very small; and may be measured in seconds, thereby allowing real-time quantification and analysis, and thus the mBFP mutant has an excellent reporter characteristic. According to an embodiment, it was confirmed that in the case of a mutant in which the His-tag was fused to the N-terminus of the mBFP protein, wherein tyrosine (Tyr, Y), which is the 157th amino acid based on the amino acid sequence (SEQ ID NO: 6) of the wild-type protein, was substituted with histidine (His, H) or asparagine (Asn, N), an activity of aldehyde dehydratase was removed while exhibiting significantly excellent NADPH-dependent fluorescence activity than other mutants, and thus the real time imaging and quantitative effect of NADPH was the most excellent.

In addition, the present disclosure also provides a nucleic acid sequence encoding the amino acid sequence of the mutant as described above.

The nucleic acid sequence is not particularly limited as long as it is a sequence capable of encoding the amino acid sequence. For example, the nucleic acid sequence may include a gene having 80% homology, preferably 85% homology, more preferably 90% homology, and most preferably 95% or more homology with the sequence represented by SEQ ID NO: 1 or 2 in consideration of degeneracy of the genetic code and amino acid conservative substitution.

Further, the present disclosure provides a recombinant expression vector including the nucleic acid sequence as described above.

The kind of plasmid for constructing the vector is not limited unless the object of the present disclosure is impaired. If the vector is constructed to efficiently express the mBFP mutant protein from the gene transformed into a host cell, a size of the vector, location of the gene, and the like are not particularly limited.

According to the present disclosure, the mBFP wild type and a mutant in which the oxidase/reductase activity are removed may be expressed by attaching a poly histidine tag to each enzyme gene enabling the use of affinity chromatography for mass separation and purification of high purity. This method may prevent a relative decrease in the yield that is generated in a method in which density gradient centrifugation, salting out, or dialysis, which is typically used for protein isolation and purification, is generally performed, and ion exchange or gel filtration chromatography is performed in multiple stages, followed by concentration.

The present disclosure also provides a transformant, excluding human, transformed with the recombinant expression vector as described above.

In the present disclosure, the transformant is not particularly limited as long as the object of the present disclosure is not impaired, but may be a microorganism, an animal cell, or a plant cell. Specific examples of the transformant according to an embodiment of the present disclosure may include *Escherichia coli, Pichia pastoris*, HeLa cell, plant callus cell, and the like.

Further, the present disclosure provides a composition for real-time quantification of NADP(H) in vivo including the mutant as described above.

The composition for real-time quantification of NADP(H) according to the present disclosure is not limited unless the object of the present disclosure is impaired, but metal ions may be added to quantify the coenzyme with higher sensitivity. The metal ion may be one or more metal ions selected from the group consisting of $Li^+$, $Hg^{2+}$, $Co^{2+}$, $Mg^{2+}$, $Mn^{2+}$, $Zn^{2+}$, $K^+$, $Ca^{2+}$, $Al^{3+}$, $Fe^{3+}$, $Fe^{2+}$, $Ag^+$, $Ni^{2+}$, $Pb^{2+}$ and $Cu^{2+}$, but is not limited thereto. According to an embodiment of the present disclosure, it is preferable to add a metal salt containing a metal ion since it is possible to increase sensitivity two times or more when quantifying NADP(H).

In addition, when the metal ion and a surfactant are added together the sensitivity may be increased three times or more when quantifying NADP(H). The surfactant may be one or more selected from the group consisting of sodium dodecyl sulfate (SDS), Na-deoxycholate, cetrimonium bromide (CTAB), dodecyl-trimethylammonium bromide (DTAB), and Triton X-100, but the kind thereof is not limited thereto.

Any surfactant generally usable in the field to which the present disclosure belongs is freely usable.

Further, the present disclosure provides a method for real-time quantification of NADP(H) including: adding the mutant together with a substrate to a NADP(H)-dependent oxidase/reductase, and measuring a fluorescence change.

The method for measuring enzyme activity according to the present disclosure is a method capable of measuring NADPH in a reaction solution in real time in seconds by adding only the mBFP mutant, and thus as compared to the existing method of using fluorescent or luminescent substrates, it is not necessary to add the additional substrate (color development or fluorescent substrate), and it is possible use the method even under oxygen-free condition and at low temperature. Therefore, the method for measuring enzyme activity according to the present disclosure has advantages of high reliability and sensitivity in measuring enzyme activity.

Further, the present disclosure provides a method for quantifying a NADP(H)-dependent oxidase/reductase including adding the mutant to a reaction solution including NADP(H)-dependent oxidase/reductase, and measuring a fluorescence change.

More specifically, the substrate is added to an oxidase/reductase having a coenzyme-dependent activity to induce the reaction, and then an amount of NADPH changed by a coupling enzyme activity such as oxidation from NADP+ to NADPH or reduction from NADPH to NADP+ in reverse is measured by fluorescence through the mBFP mutant, thereby calculating the enzyme activity (nmol/min/mg protein). This process is a feasible method since this process uses the characteristic in which a substrate consumption amount of the oxidase/reductase and a coenzyme consumption amount are consumed at the same molar ratio, thereby measuring a specific activity by the amount of changed coenzyme even when the substrate is not known. Therefore, by using the fluorescence values changed by adding the coupling enzyme and the mBFP mutant in measuring the activity of all enzymes using coenzymes NADP+ and NADPH, the specific activity of the enzyme may be accurately and quickly measured, and the measurement may be performed even under oxygen-free conditions, low-temperature, high-temperature, acidic and basic conditions. Therefore, it is possible to provide a method for enzyme quantification with high reliability and sensitivity in measuring enzyme activity.

In addition, the present disclosure provides a kit for real-time quantification of NADP(H) including the mutant.

The kit using the real-time quantification according to the present disclosure is able to diagnose diseases in real time using a coenzyme-dependent enzyme activity of an animal tissue cell in a biological sample. The real-time diagnosis may mean that the diagnosis is able to be completed with almost no waiting time for sample analysis, preferably within 1 to 15 seconds of waiting time, but the present disclosure is not limited thereto.

According to characteristic enzyme activity depending on disease, it is possible to diagnose various diseases such as heart disease, liver disease, blood disease, and the like, as well as various kinds of cancer. For example, the method for quantifying the coenzymes and the composition for quantifying the coenzymes of the present disclosure using a body fluid such as saliva, urine, or blood on a biological sample may be used to determine presence or absence of an enzyme activity as a disease marker in the sample by measuring the coenzyme-dependent enzyme activity, thereby diagnosing the diseases. Further, the present disclosure may be utilized for diagnosis of diseases such as red blood cell defeat by measuring activity of glucose-6-phosphate dehydrogenase (G6PDH) dependent on the coenzyme NADP+.

Hereinafter, exemplary embodiments of the present disclosure are described in detail. The exemplary embodiments are provided to more specifically explain the present disclosure, but the scope of the present disclosure is not limited thereto.

Experimental Materials mBEP gene: GenBank Accession No. AF485783.
pQE30 (Qiagen, USA)
*E. coli* XL1-Red (Invitrogen, USA)

[Example 1] Construction of mBFP Mutant from which Enzyme Activity is Removed

1. Production and Screening of Mutant Library

In order to remove the enzyme activity of mBEP with respect to various aldehydes which are typical substrates, random mutation was induced using mutation-inducing host *E. coli* to cause a random mutation in a specific gene.

The mBEP was cloned into a pQE30 plasmid, and the vector having 4,174 bp prepared as shown in FIG. 1 was transformed into *E. coli* XL1-Red using conventional electroporation, and then cultured for 24 hours or more for proliferation of various generations.

The culture broth was plated on a solid medium, and each of the clones produced in the form of a single colony was divided and cultured on a 96 well plate. Then, the activity of mBFP protein was measured using a fluorescent reader (M200, Tecan).

In order to measure benzaldehyde dehydrogenase activity, a reaction solution of pH 7.5 in which 100 mM Tris, 100 mM sodium chloride, 0.05% Triton X-100, 0.5 mM benzaldehyde and 0.5 mM NADPH were mixed and added at an amount of 10 μL per well containing 90 μL of cultured cells, and reacted for 10 minutes. The change in fluorescence value was measured by the fluorescence reader to measure the amount of NADPH consumed by the activity of mBFP mutant enzyme.

Figure 2:
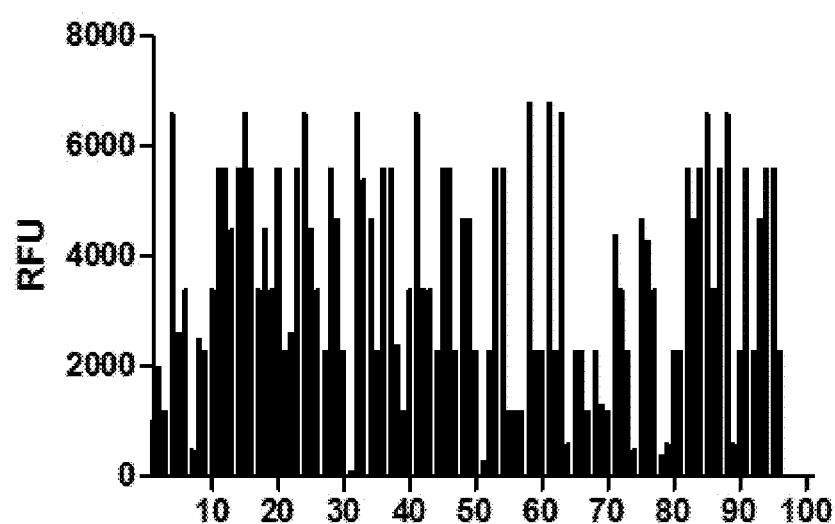
FIG. 2 shows NADPH-dependent fluorescence activities (A) and enzyme activities (B) of mutants of the blue fluorescent protein mBFP.
Figure 2:
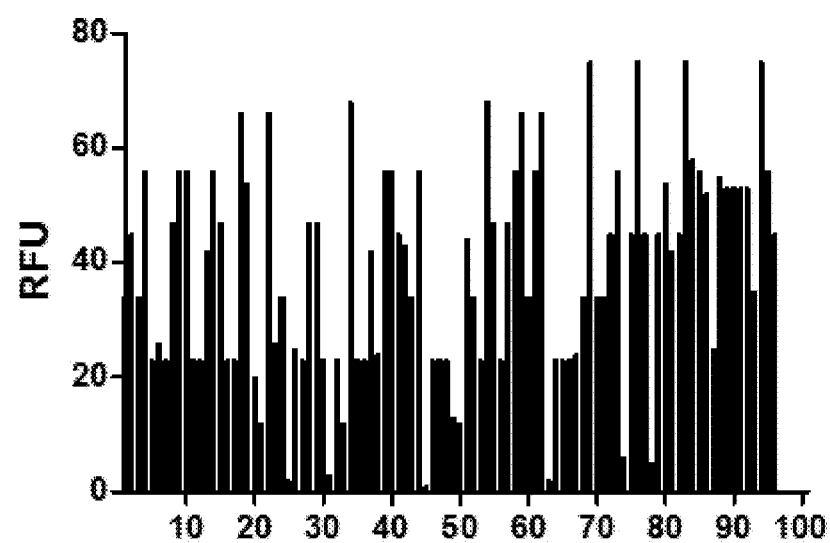

Accordingly, three mutant clones with reduced activity of aldehyde dehydrogenase were screened for mutants without the change in fluorescence as compared to initial measurement values (FIG. 2).

2. Effects of the Mutant Enzyme on the Cell Growth

Three clones screened in part 1, above, and the strain containing wild type protein were cultured, and the optical density ($OD_{600}$) was measured at 600 nm over time by the conventional method to compare growth with each other.

Figure 3:
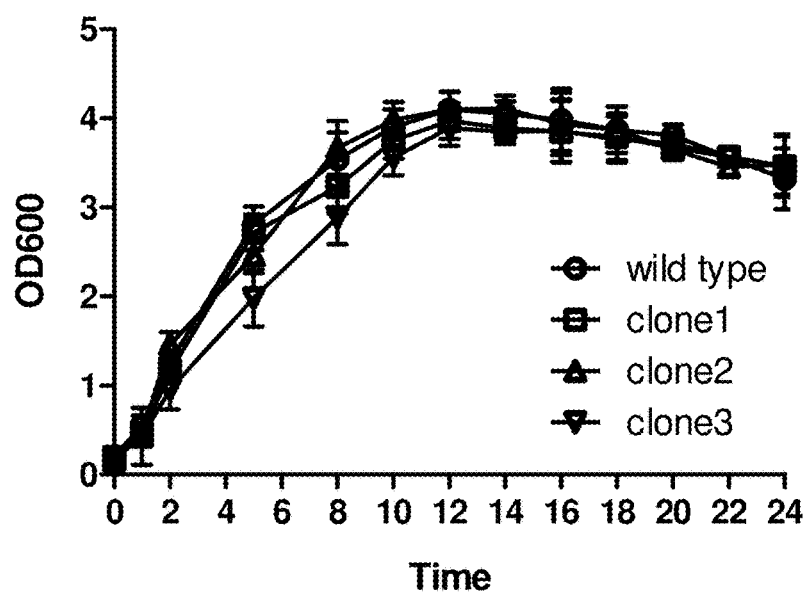
FIG. 3 shows a comparison of growth curves of the wild type mBFP and recombinant strains expressing the mutant mBFP.
Figure 4:
FIG. 4 is a photo of SDS-Page results confirming the isolation and purification of mutant blue fluorescent protein mBFP.

Results thereof are shown in FIG. 3.

From these results, the mutant strains had some differences in a rate of a growth period, but it was confirmed that the growth of the cell was not significantly different from that of the wild type when entering the stationary phase and the death phase through the exponential phase. Thus, it was confirmed that the introduction of the mutant gene did not act as a factor for inhibiting growth in the growth of recombinant cells.

3. Purification of mBEP Mutant Protein

Three kinds of the screened mutant mBFP clones were inoculated into 5 mL of liquid LB (luria-bertani) medium containing 50 μg/mL ampicillin, respectively, and pre-cultured at 37° C. and 200 rpm for 12 hours.

1 mL of the above culture fluid was inoculated into the same 100 mL medium, and main-cultured for 3 hours under the same conditions. When $OD_{600}$ value was 0.5 to 0.6, isopropyl beta-D-1-thiogalactopyranoside (IPTG) was added and further cultured for 4 hours. The cells were then recovered via high-speed centrifugation.

In order to efficiently obtain the mBFP mutant in simple steps, affinity chromatography using cibacron blue which is used for affinity chromatography of proteins binding to NADPH and affinity chromatography using His-tag, were sequentially used.

To this end, the cells recovered by the above-described method were suspended in 20 mL of binding buffer (20 mM Tris-HCl, pH 7.5), sonicated for 5 seconds using an ultrasonic crusher, and allowed to stand for 10 seconds. This process was repeated 15 times to lyse the cells.

The lysed cells were centrifuged at 10,000×g for 15 minutes to remove insoluble precipitates, and the supernatant containing soluble proteins was recovered. In order to remove macromolecular impurities present in the recovered supernatant, 1 g of cell debris remover (CDR) from Sigma-Aldrich was added per 20 mL, mixed at low temperature for 10 minutes, followed by high-speed centrifugation at 10,000×g for 45 minutes, and the resulting product was filtered through a 0.45 um syringe filter to remove any remaining impurities.

The cell lysate pretreated through the above procedure was diluted by treating the same binding buffer with 5 times volume as above. Binding of each protein to the equilibrated cibacron blue resin was induced at a flow rate of 2 mL/min, and then 100 mL of the binding buffer flowed at a flow rate of 3 mL/min to remove proteins that were not bound to the column and impurities that were nonspecifically weakly bound thereto.

The attached protein was recovered using an elution buffer (20 mM Tris-HCl, 2 M sodium chloride, pH 7.5).

After confirming the fraction in which mBFP was recovered and the purity by SDS-PAGE, chromatography using a metal-affinity resin column was performed to remove contaminant proteins eluted together. To this end, the solution containing the recovered protein was diluted 4-fold and then attachment of protein to Ni-NTA resin equilibrated with a binding buffer (20 mM Tris-HCl, 500 mM sodium chloride, pH 7.5) was induced at a flow rate of 2 mL/min.

100 mL of wash buffer (20 mM Tris-HCl, 500 mM sodium chloride, 10 mM imidazole, pH 7.5) flowed at a rate of 4 mL/min in order to remove the proteins that were not bound to the column and impurities that were nonspecifically weakly bound thereto. Then, the protein adsorbed to the Ni-NTA resin was recovered using an elution buffer (20 mM Tris-HCl, 500 mM sodium chloride, 250 mM imidazole, pH 7.5).

After confirming the fractional section using a fluorescence spectrophotometer, a desalting column was used to remove imidazole and salts present in the eluate. The purity of proteins in recovered solution was confirmed by SDS-PAGE Results thereof were shown in FIG. 6.

From this, it was confirmed that a protein having a high purity of 95% or more was isolated.

4. Activity of Purified Mutant mBFP

In order to measure the enzyme activity of the mutant mBFP protein isolated through the above procedure, the NADPH-dependent fluorescence activity was measured as follows.

Each 10 uM purified mutant mBFP protein was dispensed into 96-well plates, 500 uM NADPH was added at an amount of 10 μL per well, and then fluorescence was measured.

As a result, it was confirmed that there was little change in fluorescence or the fluorescence reduction was as low as 15% or less as compared with the wild type protein. From these results, it was confirmed that even if it was a mutant having a difference in activity, the mutant possessed NADPH-dependent fluorescence ability.

In order to measure the enzyme activity of the short-chain dehydrogenase/reductase family (SDR family) of the purified mutant mBFP, a reaction solution (100 mM Tris, 100 mM sodium chloride, 0.05% Triton X-100, 0.5 mM benzaldehyde, 0.5 mM NADPH, pH 7.5) for measuring aldehyde dehydrogenase was added at an amount of 10 μL to each well to which the protein was added, and reacted for 10 minutes, and then the amount of reduced NADPH was measured using a fluorescent reader.

As a result, it was confirmed that the aldehyde dehydrogenase activity was mostly removed from two clones of mutant proteins. In the following experiment, among the clones, mBFP2, which is a clone in which the NADPH-dependent fluorescence activity was the highest and the activity of aldehyde dehydrogenase was removed as shown in Table 1 below, was selected and used.

TABLE 1

| Enzyme activity of mutant mBFP | | | | |
| --- | --- | --- | --- | --- |
| U mg$^{-1}$ | Pivaldehyde | Acetaldehyde | Benzaldehyde | Hexanal |
| Wild type | 14.43 ± 0.68 | 10.34 ± 0.24 | 6.41 ± 0.34 | 4.34 ± 0.14 |
| mBFP1 | 4.82 ± 0.25 | 3.32 ± 0.12 | 0.76 ± 0.02 | Not detected |
| mBFP2 | Not detected | Not detected | Not detected | Not detected |
| mBFP3 | 2.43 ± 0.68 | 0.22 ± 0.05 | Not detected | Not detected |

[Example 2] Expression of Transformation of mBFP and Activity Confirmation

1. Expression Vector Construction

Primers for expression of mBFP were produced as shown in Table 2, and polymerase chain reaction (PCR) was performed.

TABLE 2

| Name | Sequence |
| --- | --- |
| X-BFP F | SEQ ID NO. 7<br>AATCTAGAATGCAGAATCTGAACGGCAAAGTG |
| X-BFP R | SEQ ID NO. 8<br>AAGAATTCTTAAGCGGCGAAGCCGCCGT |
| HcC-BFP F | SEQ ID NO. 9<br>ATAGAATTCATGCAGAATCTGAACGGCAAAGTG |
| Hc-BFP R | SEQ ID NO. 10<br>ATAGCGGCCGCTTAAGCGGCGAAGCCGCCG |
| C-BFP R | SEQ ID NO. 11<br>AATCTAGATTAAGCGGCGAAGCCGCCGT |

The PCR was performed for a total of 30 cycles with denaturation at 95° C. for 30 seconds, annealing at 58° C. for 45 seconds, and extension at 72° C. for 90 seconds.

The genes amplified with each primer pair were cloned into plasmids pXMJ19, pPICHoLi, pCDNA3.1 and pCAMBIA, respectively, using the homologous gene recombination kit (in-fusion HD cloning kit manufactured by Clontech in U.S.A) to produce recombinant vectors pXMJ19-mBFP, pPICHoLi-mBFP, pCDNA3.1-mBFP and pCAMBIA-mBFP, respectively.

2. Transformation Method

Transformation of Recombinant Vector pXMJ19-mBFP into *Corynebacterium glutamicum*

The competent cell of the *Corynebacterium glutamicum* was produced as follows.

The *Corynebacterium glutamicum* was cultured in LB (luria-bertani) medium, and then single colony was inoculated into an LB (luria-bertani) medium containing 2% glucose and pre-cultured, and 1 to 2% of the culture fluid was inoculated into an Epo medium containing isonicotinic acid hydrazide (4 μg/mL isoniazid, 25 μg/mL glycine, 0.1% Tween 80), and cultured at 25° C. and recovered when an optical density at 600 nm was 0.6. The resulting product was washed four times with 10% glycerol to produce an electrocompetent cell.

The produced cells were divided into 100 μL aliquots and stored at −80° C. until used.

In order to improve the transformation yield of the *Corynebacterium glutamicum*, a recombinant vector in which a phenomenon that a recombinant gene is unstable due to a methylation pattern by transformation into *E. coli* strain JM110, was recovered and used.

The recombinant plasmid (200 to 500 ng/μL) was added to 100 μL of the electrocompetent cell, and the current was applied in an electroporation device (Bio-Rad, U.S.A.) under the conditions of a 0.2 cm cuvette, 25 uF, 600 Ω, 2.5 kV and 10-12 nm. These cells were subjected to rapid quenching from 46° C. to 6° C., and heat shock was applied thereto (van der Rest M E et al., Appl. Microbiol. Biotechnol., 52:541-545, 1999).

Subsequently, 1 mL of SOC medium (Sigma-Aldrich) was added thereto and the cell was cultured at 32° C. for 1.5 hours. The recombinant strains were screened by plating on a solid medium containing an ampicillin antibiotics.

2) Transformation of recombinant Vector pPICHoLi-mBFP into *Pichia pastoria*

A competent cell of *Pichia pastoris* was produced as follows.

*Pichia pastoris* (GS115) was inoculated into 10 mL of yeast extract-peptone-dextrose (YPD) medium (Sigma-Aldrich) and cultured overnight at 30° C. Then, 0.2 mL of the culture was inoculated into 100 mL YPD medium, and cultured until the optical density at 600 nm was 1.0.

The culture was centrifuged at 2500×g for 5 minutes at 4° C., suspended in 100 ml of cold sterilized distilled water, and centrifuged under the same conditions. The same procedure was repeated with 50 ml of cold sterilized distilled water to produce a competent cell having a final volume of 0.5 mL.

The DNA was linearized by cleavage with Avr1 restriction enzyme. Then, 80 μL of competent cell produced above and 10 μg of the linearized DNA were mixed and placed in a 0.2 cm electroporation cuvette. After standing in ice for 5 minutes, the product was transformed by electroporation at 1,500 Volt and 200Ω.

Thereafter, 1 mL of 1 M sorbitol was immediately poured and mixed, transferred to a sterilized microcentrifuge tube, applied to a YPD/zeosin plate, and cultured at 30° C. until a colony was formed, and the recombinant strain was screened.

3) Transformation of Recombinant Vector pCDNA3.1-mBFP into Animal Cell (HeLa Cell)

The animal cell was cultured in DMEM (Dulbecco's modified Eagle's medium, Thermo Fisher Scientific, USA) containing 10% fetal bovine serum. The cultured cell was dispensed into a 6-well plate, and the next day, the cultured cell was mixed with 2 μg of the expression vector in the presence of lipofectamine 2000 (Invitrogen) as a transfection agent, and reacted for 20 minutes.

After 8 hours, the medium was removed, washed three times with a phosphate-buffered saline (PBS) buffer (WelGene Inc.), and then replaced with DMEM medium containing only 10% fetal bovine serum. The cell was further cultured at 37° C. in a 5% $CO_2$ atmosphere for 48 hours to obtain a transduced cell.

4) Transformation of Recombinant Vector pCAMBIA-mBFP into Plant Cell (Callus)

The mBFP gene inserted into the plasmid plant vector (pCAMBIA1300) was transformed into the *Agrobacterium* EHA105 strain using the *Agrobacterium* method, and then cultured in an LB medium supplemented with 50 mg/L of the antibiotic kanamycin at 28° C. for 2 days.

*Agrobacterium* was suspended in an EME liquid medium (pH 5.2) supplemented with 100 µM of acetosyringone when the concentration of the *Agrobacterium* strain was about 0.5 according to the measurement of the optical density at 600 nm, and then cultured with a callus cell at 28° C. and 100 rpm for 20 minutes.

The cultured callus cell was collected by a mesh, dried in a sterilized filter paper, placed in an EME medium supplemented with 8% agar in which the pH was adjusted to 5.2, and then cultured in a dark room in an incubator at 25° C. for 5 days.

The prepared callus cell was cultured at 100 rpm for 2 weeks in EME medium (pH 5.7) supplemented with 10 mg/L hygromycin and 250 mg/L cefotaxime. After 2 weeks, the callus cell collected using the mesh was placed in EME medium supplemented with 70 g/L lactose, 250 mg/L cefotaxime, 25 mg/L hygromycin, and 1.8% agar (pH 5.8), and cultured. After four weeks, green somatic embryo was selected.

The screened somatic embryo was placed in MT base medium supplemented with 1 mg/L gibberellic acid, 34 mg/L adenine, 500 mg/L malt extract, and 0.2% gelrite (pH 5.8) and cultured for 8 weeks in a dark room to induce a transformed callus cell from the transformed somatic embryo.

3. Expression and Fluorescence of mBFP Protein

1) Cell Culture

Each of the transformed cells was cultured in the following manner.

Culture of *Escherichia coli*

*Escherichia coli* was cultured in an LB medium containing antibiotics as in part 3 of Example 1.

Culture of *Corynebacterium glutamicum*

*Corynebacterium glutamicum* strain was streaked on an LB medium plate containing antibiotics in an anaerobic jar sealed together with a carbon dioxide generating kit (OXOID Limited Kit, UK) for culturing under anaerobic conditions, and then cultured overnight at 37° C.

The cell was then inoculated into a 17.5 mL tube (Hungate tube, Belcoglass, U.S.A.) completely filled with argon, and cultured.

Culture of Animal Cell

The transformed animal cell was cultured in DMEM medium containing 10% fetal bovine serum at 37° C. and 5% $CO_2$ for one day.

Culture of *Pichia pastoris*

The transformed *Pichia pastoris* was cultured in a BNK medium (1.34% yeast nitrogen base, $4\times10^{-5}$% biotin, 1% glycerol, 0.1 M K-phosphate, pH 6.0) at 250 rpm at 30° C. for one day. Then, the cell was transferred to BMM medium (1.34% yeast nitrogen base, $4\times10^{-5}$% biotin, 0.5% methanol, 0.1 M K-phosphate, pH 6.0) and cultured with 0.5% methanol added daily.

Culture of Callus

The transformed callus was prepared by adding 22 g of transformed callus cell to 100 mL of a suspension medium to which 50 g/L of sucrose was added to Murashige-Tucker (MT) medium, and cultured at 15° C. and 150 rpm for one day.

2) Confirmation of mBFP Expression in Transformed Cell

Figure 5:
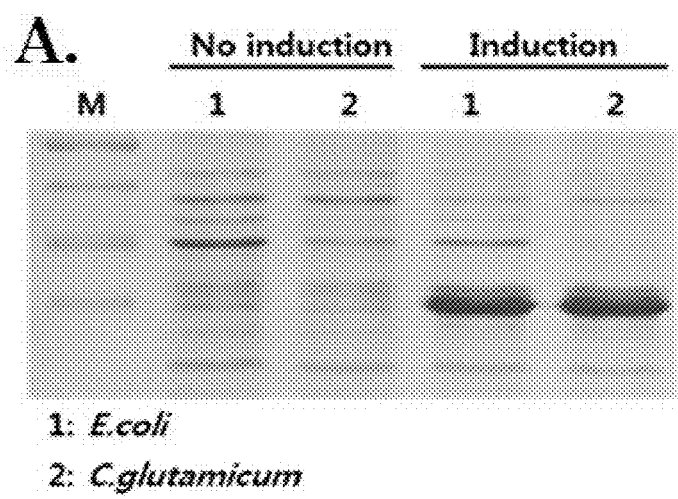
FIGS. 5 A and B show a photo of SDS-PAGE results in which the mutant blue fluorescent protein mBFP is expressed in *E. coli*, *C. glutamicum*, HeLa cells and plant callus cells.
Figure 5:
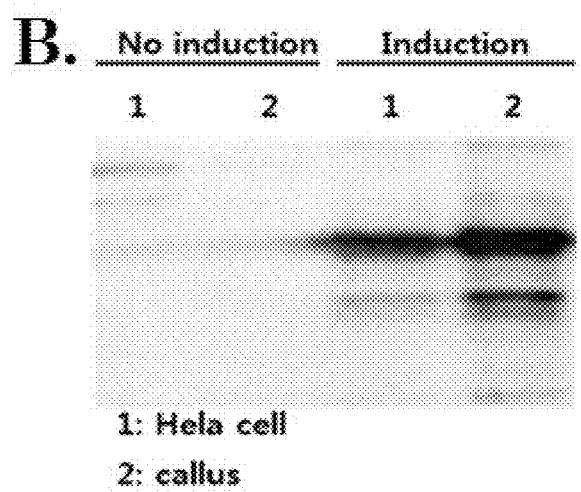

In order to confirm the mBFP protein expression of the cells, conventional SDS-PAGE and western blotting were used. Results thereof are shown in FIGS. 5A and 5B.

As a result, it was confirmed that the mBFP protein was expressed in each cell.

The cultured cells were disrupted, recovered, and purified using the His-tag as follows.

The cell supernatant disrupted with phosphate buffered saline (PBS) was injected into and passed through Ni-NTA Spin Columns (Qiagen), and washed with wash buffer (PBS, 10 mM imidazole). Then, the mBFP protein was recovered with the elution buffer (PBS, 100 mM imidazole).

The mBFP purified in each cell was injected into a 96-well plate and reacted with NADPH, and then fluorescence was measured.

Figure 6:
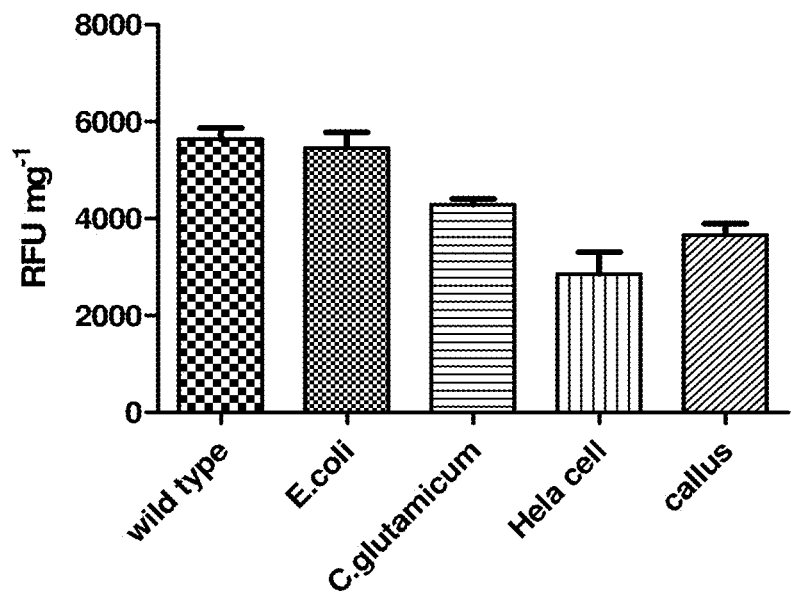
FIG. 6 shows a quantification of fluorescence activity with respect to the results expressed in FIG. 5.

Results thereof are shown in FIG. 6.

From these results, it was confirmed that the purified mBFP exhibited NADPH-dependent fluorescence activity even though there was a difference in the intensity of fluorescence activity according to the type of each cell.

3) Reductase Activity of Mutant mBFP Protein

In order to confirm whether the mBFP protein had activity as a reductase through mutation, the reductase activity of mBFP was measured using the reaction solution for measuring the benzaldehyde reductase activity of Example 1 above.

Figure 7:
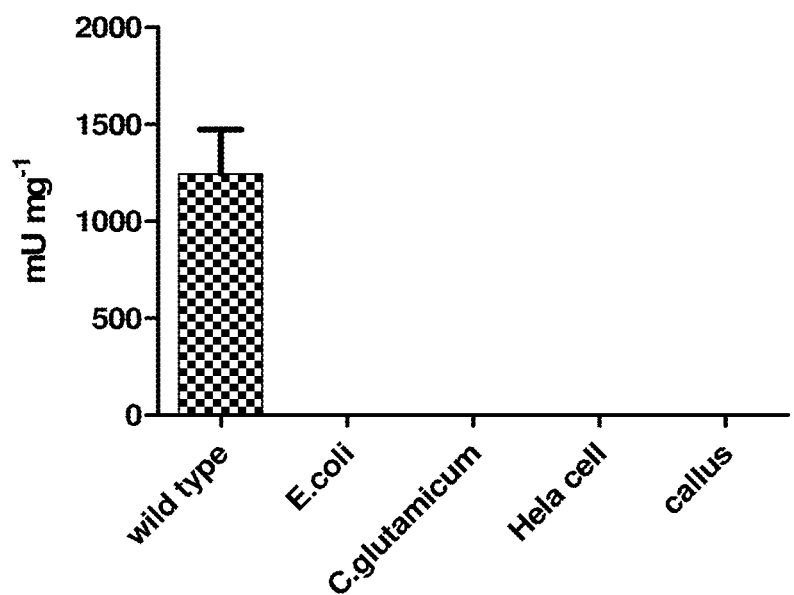
FIG. 7 shows measuring quantification of reductase activity with respect to the results expressed in FIG. 5.

Results thereof are shown in FIG. 7.

From these results, it was confirmed that the wild type exhibited the reductase activity, but each activity as the reductase was removed from the mutant mBFP protein according to the present disclosure.

From the above-described results, it was confirmed that the mutated mBFP protein exhibited NADPH-dependent fluorescence activity in various kinds of cells, respectively, and was easy to be expressed to have an advantage of being utilized as a general bioreporter.

[Example 3] NADPH Imaging by Intracellular mBFP Protein

1. Intracellular NADPH Imaging

In order to confirm the mBFP fluorescence activity in the animal cell, images were continuously taken in units of 1 frame per second while screening in units of 10 nm using a two-photon microscopy.

Figure 8:
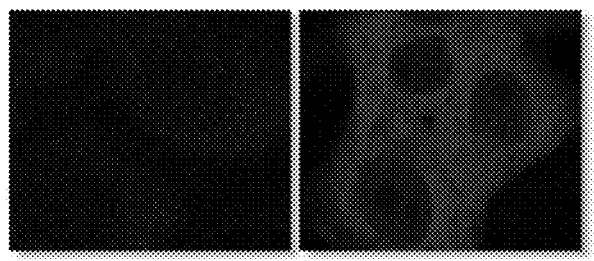
FIG. 8 shows fluorescence images of animal cells in which the mutant blue fluorescent protein mBFP is expressed, using a two-photon microscope.

Results thereof are illustrated in FIG. 8.

From these results, it could be confirmed that the fluorescence activity was clearer than that of the control group, and even if continuous observation was performed, there was no problem such as inhibition of cell growth or change in fluorescence value.

Thus, it was possible to solve all of the difficulties of continuous observation due to a low resolution problem when using a conventional fluorescence microscope or an inhibition problem of cell growth according to laser irradiation having a short wavelength when using a confocal laser scanning microscope for obtaining a higher resolution.

In addition, when the two-photon microscopy was used, since the excitation wavelength was twice as high as in the conventional case, stimulation with weak energy could be applied to have a small effect on cells, and be capable of continuously confirming the mBFP fluorescence activity in the cells. Thus, it is considered that easy measurement of NADPH could be performed.

2. Evaluation of Reproducibility and Quantitative Measurement of Intracellular NADPH Imaging 1) Dependence on Fluorescence and NADPH The recombinant animal cells produced in the Examples above were treated with diamide, which is an oxidant, to reduce the amount of NADPH in the cells, and the change in fluorescence was observed as follows.

First, before observing the recombinant animal cells, the medium was replaced with a culture medium from which glucose was removed to prevent continuous overproduction of NADPH, and the cells were cultured for 1 hour and images thereof were observed.

After treatment with 40 μM diamide, fluorescence images were taken every second using a real-time image measurement method using a two-photon microscopy.

Figure 9:
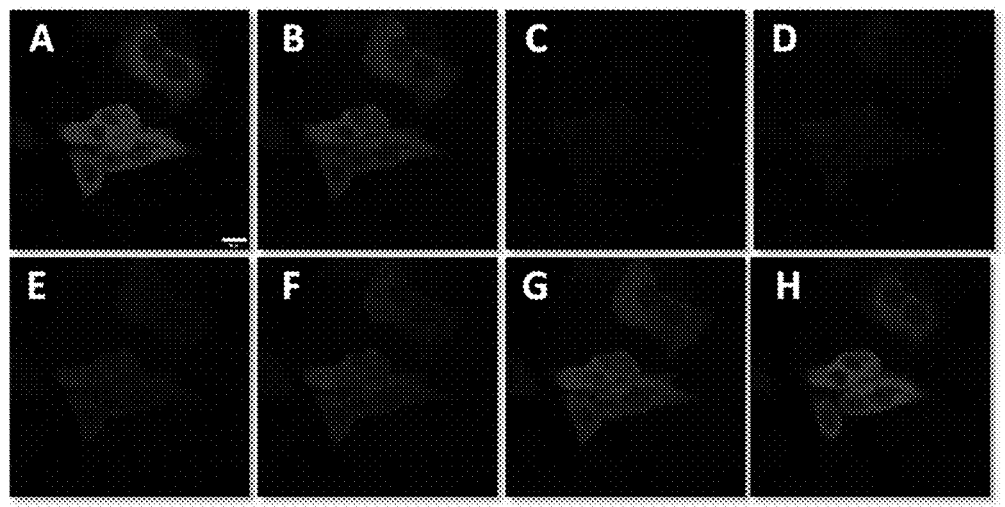
FIG. 9 A-H show coenzyme fluorescence images over time using a two-photon microscope by treating animal cells in which the mutant blue fluorescent protein mBFP is expressed with a specific oxidizer and a graph I of the normalized intensity shown in the coenzyme fluorescence images.
Figure 9:
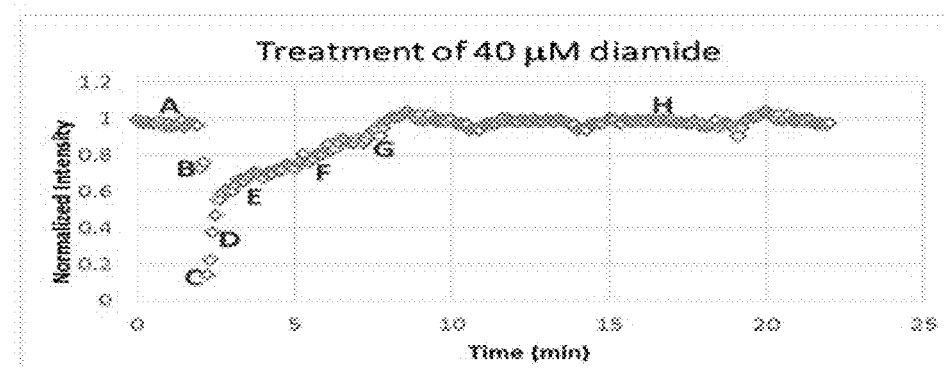

Results thereof are shown in FIG. 9.

From these results, it was confirmed that when the diamide as an oxidant was treated at the above-described concentration, the fluorescence intensity rapidly decreased after a predetermined time elapsed, and as the concentration of the oxidant decreased and the NADPH concentration increased, the fluorescence was gradually recovered. From this, it was confirmed that the intensity of the fluorescence image was dependent on the amount of NADPH by intracellular mBFP.

2) Quantitative Measurement of Fluorescence Intensity and Amount of NADPH

Glucose, glutamate, malate, succinate, pyruvate, lactate, and glucose-6-phosphate (G6P) as substrates for culturing animal cells were supplied to each medium, and the animal cells were cultured, and each substrate was added thereto. The amount of NADPH was quantified using the NADP(H) assay kit (Sigma Aldrich, U.S.A.), compared with the fluorescence level measured by the microscopy, and the amount of change in NADPH according to the change in fluorescence intensity was measured.

Figure 10:
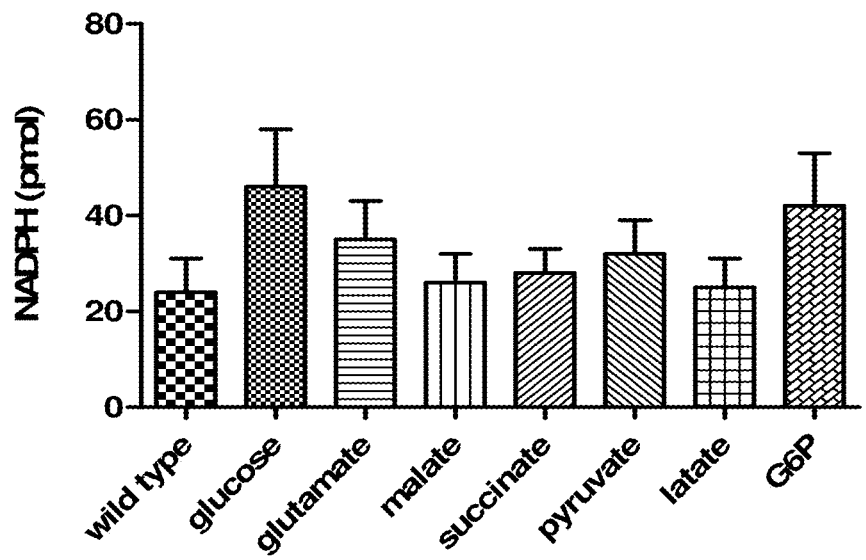
FIG. 10 shows the change in an amount of NADPH expressing the mutant blue fluorescent protein mBFP according to the type of substrate added to the culture medium.

Results thereof are shown in FIG. 10.

Figure 11:
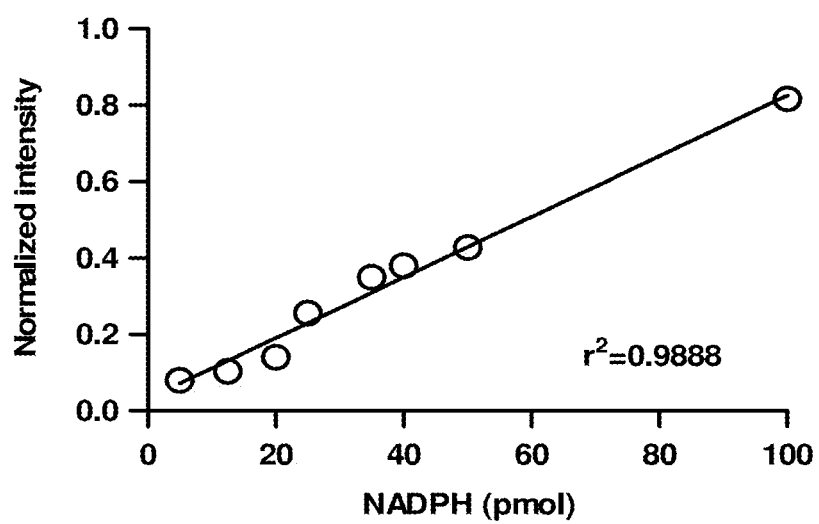
FIG. 11 is a graph showing the quantification of fluorescence of animal cells in which the mutant blue fluorescent protein mBFP is expressed.

From these results, it could be appreciated that the amount of change in NADPH was the largest when glucose was used as substrate. The correlation of the amount of change in NADPH according to the amount of change in fluorescence intensity was analyzed by a conventional regression analysis, and as a result, it was confirmed that linear correlation distribution was shown (FIG. 11). In other words, it was confirmed through the analysis that the fluorescence intensity in cells was linearly dependent on the amount of NADPH by mBFP.

[Example 4] Coenzyme-Dependent Metabolism-Based NADPH Imaging

The mBFP-transformed animal cells were cultured and treated with NADPH dehydrogenase inhibitors shown in Table 3, respectively, and the amount of change in NADPH was measured.

TABLE 3

NADPH dehydrogenase inhibitor

| Inhibitor | Related enzyme |
|---|---|
| Dehydroepiandrosterone; DHEA | Glucose-6-phosphate dehydrogenase |
| Auranofin | Thioredoxin reductase(TrxR) |
| AGI-6780 (CAS No. 1432660-47-3) | Isocitrate dehydrogenases |
| Galloflavin | Lactate dehydrogenase |
| Methylmalonate; MMA | Succinate dehydrogenase |
| CPI-613 (CAS No. 95809-78-2) | Pyruvate dehydrogenase |
| 6-Aminonicotinamide; 6-ANA | 6-phosphogluconate dehydrogenase |
| R162 (CAS No. 64302-87-0) | Glutamate dehydrogenase |

Figure 12:
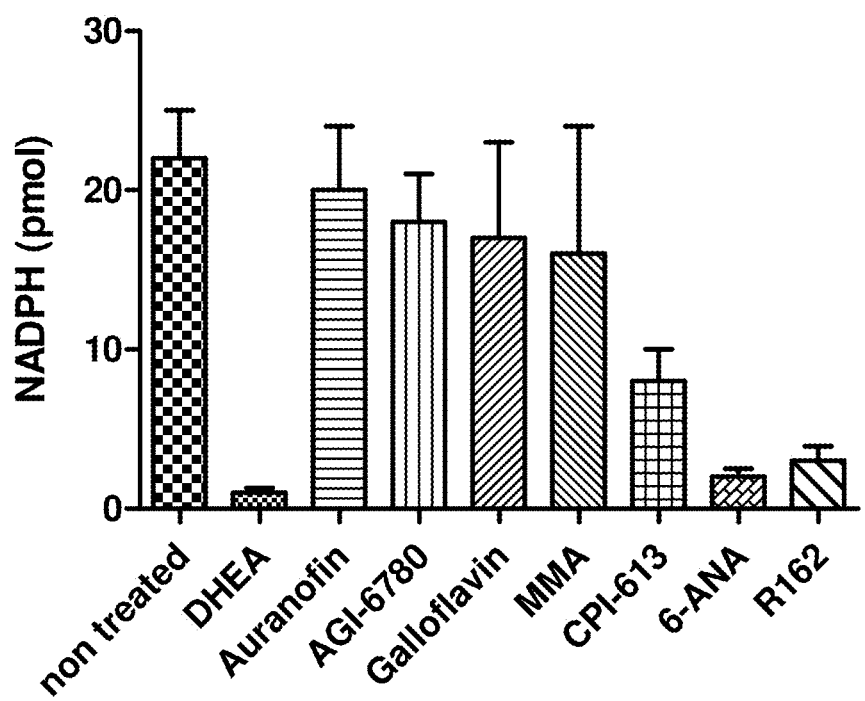
FIG. 12 is a chart showing the change in the amount of NADPH when an enzyme inhibitor is treated in animal cells in which the mutant blue fluorescent protein mBFP is expressed.

FIG. 12 shows results of quantifying NADPH by measuring the real-time images after treatment with the inhibitor and then measuring the changed fluorescence intensity.

From these results, it was confirmed that the difference of fluorescence intensity due to mBFP was the largest when glucose-related enzyme was inhibited by treatment with DHEA, 6-ANA, or the like, and the change in NADPH amount also showed the same pattern as the change in fluorescence intensity.

[Example 5] Comparison of Stability of Coenzyme Measurement with Existing Wild-Type mBFP, or his- and Ramp Tag Derivatives The stability of the analysis system was compared by continuously measuring the change in fluorescence value according to the coenzyme NADPH measured in real time using the mBFP mutants (Y157H and Y157N) of the present disclosure as a predetermined period of time elapsed. In the present experiment, the analysis was performed by treating the wild-type mBFP of the related art and His- and Ramp-mBFP at the same amount under the above-described reaction conditions.

Figure 13:
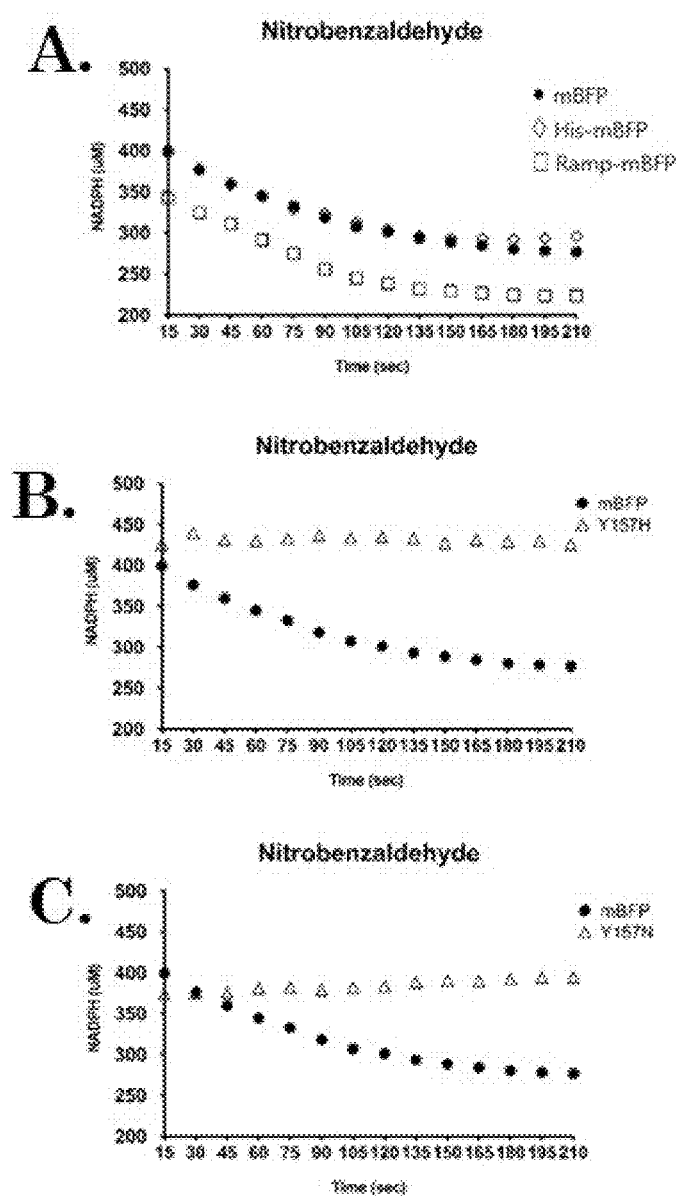
FIG. 13 A-C are graphs showing quantitative values which are stably measured when the amount of NADPH in the cell is continuously measured since unlike wild type or existing derivatives, the mutant blue fluorescent protein mBFP of the present disclosure does not have enzyme activity due.

As a result, as shown in FIG. 13, it was confirmed that unlike the existing wild type or derivatives, the mutant of the present disclosure was a stable system in which the inherent enzyme activity was completely removed and the coenzyme measurement values did not change as time elapsed. On the contrary, the existing protein showed unstable characteristics in which the coenzyme was consumed by the intrinsic enzyme activity and the various aldehydes present in the biological sample, thereby reducing the fluorescence value.

Therefore, unlike a pure reaction solution in which constituent components were relatively confirmed, when using an in vivo environment or an unpurified extract composed of complex components, the present inventors found that it was possible to perform stable and accurate quantification of coenzyme and imaging in real time only when the mutant of the present disclosure was used, and completed the present disclosure.

The method for real-time quantification of a coenzyme according to the present disclosure may quantify NADP(H) as a coenzyme in real time in seconds, may quantify the coenzyme even under low temperature, acidic/basic conditions in which the enzyme activity is lowered, and may accurately and rapidly quantify the coenzyme with high sensitivity even if the concentration of the coenzyme contained in the sample is low. In particular, the method of imaging and quantifying the coenzyme contained in various biological samples may be performed by improving fluorescence in a short time even under anaerobic conditions, without adding a substrate required for coenzyme measurement or conversion without destroying cells, and without consuming the time required for formation of a special structure (fluorophore) for generating fluorescence unlike the existing quantitative systems.

Further, the NADP(H) image analysis method according to the present disclosure shows a high expression rate in various hosts to be adapted as a reporter that does not inhibit cell growth, and thus it is expected that the metabolism is able to be confirmed in real time.

What is claimed is:

1. A mutant of a blue fluorescent protein metagenome-derived blue fluorescent protein mBFP consisting of an amino acid sequence of SEQ ID NO: 1 or SEQ ID NO: 2.

2. A nucleic acid sequence encoding the amino acid sequence of the mutant of claim 1.

3. A recombinant expression vector comprising the nucleic acid sequence of claim 2.

4. A transformant, excluding human, transformed with the recombinant expression vector of claim 3.

5. The transformant of claim 4, wherein the transformant is a microorganism, an animal cell, or a plant cell.

6. The transformant of claim 5, wherein the transformant is *Escherichia coli, Pichia pastoris*, HeLa cell, or callus cell.

7. A method for quantifying NADP(H)- comprising:
adding a mutant of a blue fluorescent protein mBFP consisting of an amino acid sequence of SEQ ID NO: 1 or SEQ ID NO: 2 to a NADP(H)-dependent oxidase/reductase, and measuring a fluorescence change.

8. The method of claim 7, wherein the NADP(H) is quantified in real time.

9. The method of claim 7, wherein the amount of NADP(H) is correlated from quantifying a fluorescence change in NADP(H) oxidase/reductase to which the mutant of blue fluorescent protein mBFP has been added.

10. The method of claim 7, wherein the NADP(H) is quantified in vivo.

11. A kit for real-time quantification of NADP(H) comprising:
a mutant of a blue fluorescent protein mBFP consisting of an amino acid sequence of SEQ ID NO: 1 or SEQ ID NO: 2.

12. The kit of claim 11, wherein the real time means that analysis is performed until 1 to 15 seconds elapse.

* * * * *

```
                        SEQUENCE LISTING

<160> NUMBER OF SEQ ID NOS: 11

<210> SEQ ID NO 1
<211> LENGTH: 261
<212> TYPE: PRT
<213> ORGANISM: Artificial Sequence
<220> FEATURE:
<223> OTHER INFORMATION: mBFP Y157H with his-tag

<400> SEQUENCE: 1

Met Arg Gly Ser His His His His His His Gly Ser Ala Cys Gln Asn
1               5                   10                  15

Leu Asn Gly Lys Val Ala Phe Val Thr Gly Gly Ser Arg Gly Ile Gly
            20                  25                  30

Ala Ala Ile Val Arg Arg Leu Ala Ala Asp Gly Ala Asp Ile Ala Phe
        35                  40                  45

Thr Tyr Val Ser Ala Ser Ser Lys Asn Val Ala Thr Ala Leu Val Gln
    50                  55                  60

Glu Leu Glu Ala Lys Gly Arg Arg Ala Arg Ala Ile Gln Ala Asp Ser
65                  70                  75                  80

Ala Asp Pro Ala Gln Val Arg Gln Ala Val Glu Gln Ala Ile Val Gln
                85                  90                  95

Leu Gly Pro Val Asp Val Leu Val Asn Asn Ala Gly Ile Phe Leu Ala
            100                 105                 110

Gly Pro Leu Gly Glu Val Thr Leu Asp Asp Tyr Glu Arg Thr Met Asn
        115                 120                 125

Ile Asn Val Arg Ala Pro Phe Val Ala Ile Gln Ala Ala Gln Ala Ser
    130                 135                 140

Met Pro Asp Gly Gly Arg Ile Ile Asn Ile Gly Ser Cys Leu Ala Glu
145                 150                 155                 160

Arg Ala Gly Arg Ala Gly Val Thr Leu His Ala Ala Ser Lys Ser Ala
                165                 170                 175

Leu Leu Gly Met Thr Arg Gly Leu Ala Arg Asp Leu Gly Ala Arg Gly
            180                 185                 190

Ile Thr Ala Asn Val Val His Pro Gly Pro Ile Asp Thr Asp Met Asn
        195                 200                 205

Pro Ala Asp Gly Glu Arg Ser Gly Glu Leu Val Ala Val Leu Ser Leu
    210                 215                 220

Pro His Tyr Gly Glu Val Arg Asp Ile Ala Gly Met Val Ala Phe Leu
225                 230                 235                 240

Ala Gly Pro Asp Gly Arg Tyr Val Thr Gly Ala Ser Leu Ala Val Asp
                245                 250                 255

Gly Gly Phe Ala Ala
            260

<210> SEQ ID NO 2
<211> LENGTH: 261
<212> TYPE: PRT
<213> ORGANISM: Artificial Sequence
<220> FEATURE:
<223> OTHER INFORMATION: mBFP Y157N with his-tag
```

-continued

```
<400> SEQUENCE: 2

Met Arg Gly Ser His His His His His Gly Ser Ala Cys Gln Asn
1               5                   10                  15

Leu Asn Gly Lys Val Ala Phe Val Thr Gly Gly Ser Arg Gly Ile Gly
            20                  25                  30

Ala Ala Ile Val Arg Arg Leu Ala Ala Asp Gly Ala Asp Ile Ala Phe
        35                  40                  45

Thr Tyr Val Ser Ala Ser Ser Lys Asn Val Ala Thr Ala Leu Val Gln
    50                  55                  60

Glu Leu Glu Ala Lys Gly Arg Arg Ala Arg Ala Ile Gln Ala Asp Ser
65                  70                  75                  80

Ala Asp Pro Ala Gln Val Arg Gln Ala Val Glu Gln Ala Ile Val Gln
                85                  90                  95

Leu Gly Pro Val Asp Val Leu Val Asn Asn Ala Gly Ile Phe Leu Ala
            100                 105                 110

Gly Pro Leu Gly Glu Val Thr Leu Asp Asp Tyr Glu Arg Thr Met Asn
        115                 120                 125

Ile Asn Val Arg Ala Pro Phe Val Ala Ile Gln Ala Ala Gln Ala Ser
    130                 135                 140

Met Pro Asp Gly Gly Arg Ile Ile Asn Ile Gly Ser Cys Leu Ala Glu
145                 150                 155                 160

Arg Ala Gly Arg Ala Gly Val Thr Leu His Ala Ser Lys Ser Ala
                165                 170                 175

Leu Leu Gly Met Thr Arg Gly Leu Ala Arg Asp Leu Gly Ala Arg Gly
            180                 185                 190

Ile Thr Ala Asn Val Val His Pro Gly Pro Ile Asp Thr Asp Met Asn
    195                 200                 205

Pro Ala Asp Gly Glu Arg Ser Gly Glu Leu Val Ala Val Leu Ser Leu
210                 215                 220

Pro His Tyr Gly Glu Val Arg Asp Ile Ala Gly Met Val Ala Phe Leu
225                 230                 235                 240

Ala Gly Pro Asp Gly Arg Tyr Val Thr Gly Ala Ser Leu Ala Val Asp
                245                 250                 255

Gly Gly Phe Ala Ala
            260

<210> SEQ ID NO 3
<211> LENGTH: 261
<212> TYPE: PRT
<213> ORGANISM: Artificial Sequence
<220> FEATURE:
<223> OTHER INFORMATION: mBFP Y157 with his-tag

<400> SEQUENCE: 3

Met Arg Gly Ser His His His His His Gly Ser Ala Cys Gln Asn
1               5                   10                  15

Leu Asn Gly Lys Val Ala Phe Val Thr Gly Gly Ser Arg Gly Ile Gly
            20                  25                  30

Ala Ala Ile Val Arg Arg Leu Ala Ala Asp Gly Ala Asp Ile Ala Phe
        35                  40                  45

Thr Tyr Val Ser Ala Ser Ser Lys Asn Val Ala Thr Ala Leu Val Gln
    50                  55                  60

Glu Leu Glu Ala Lys Gly Arg Arg Ala Arg Ala Ile Gln Ala Asp Ser
65                  70                  75                  80

Ala Asp Pro Ala Gln Val Arg Gln Ala Val Glu Gln Ala Ile Val Gln
```

```
                        85                  90                  95
Leu Gly Pro Val Asp Val Leu Val Asn Asn Ala Gly Ile Phe Leu Ala
                100                 105                 110

Gly Pro Leu Gly Glu Val Thr Leu Asp Asp Tyr Glu Arg Thr Met Asn
            115                 120                 125

Ile Asn Val Arg Ala Pro Phe Val Ala Ile Gln Ala Ala Gln Ala Ser
        130                 135                 140

Met Pro Asp Gly Gly Arg Ile Ile Asn Ile Gly Ser Cys Leu Ala Glu
145                 150                 155                 160

Arg Ala Gly Arg Ala Gly Val Thr Leu Tyr Ala Ala Ser Lys Ser Ala
                165                 170                 175

Leu Leu Gly Met Thr Arg Gly Leu Ala Arg Asp Leu Gly Ala Arg Gly
                180                 185                 190

Ile Thr Ala Asn Val Val His Pro Gly Pro Ile Asp Thr Asp Met Asn
            195                 200                 205

Pro Ala Asp Gly Glu Arg Ser Gly Glu Leu Val Ala Val Leu Ser Leu
        210                 215                 220

Pro His Tyr Gly Glu Val Arg Asp Ile Ala Gly Met Val Ala Phe Leu
225                 230                 235                 240

Ala Gly Pro Asp Gly Arg Tyr Val Thr Gly Ala Ser Leu Ala Val Asp
                245                 250                 255

Gly Gly Phe Ala Ala
                260

<210> SEQ ID NO 4
<211> LENGTH: 248
<212> TYPE: PRT
<213> ORGANISM: Artificial Sequence
<220> FEATURE:
<223> OTHER INFORMATION: mBFP Y157H w/o his-tag

<400> SEQUENCE: 4

Met Gln Asn Leu Asn Gly Lys Val Ala Phe Val Thr Gly Gly Ser Arg
1               5                   10                  15

Gly Ile Gly Ala Ala Ile Val Arg Arg Leu Ala Ala Asp Gly Ala Asp
            20                  25                  30

Ile Ala Phe Thr Tyr Val Ser Ala Ser Ser Lys Asn Val Ala Thr Ala
        35                  40                  45

Leu Val Gln Glu Leu Glu Ala Lys Gly Arg Arg Ala Arg Ala Ile Gln
    50                  55                  60

Ala Asp Ser Ala Asp Pro Ala Gln Val Arg Gln Ala Val Glu Gln Ala
65                  70                  75                  80

Ile Val Gln Leu Gly Pro Val Asp Val Leu Val Asn Asn Ala Gly Ile
                85                  90                  95

Phe Leu Ala Gly Pro Leu Gly Glu Val Thr Leu Asp Asp Tyr Glu Arg
            100                 105                 110

Thr Met Asn Ile Asn Val Arg Ala Pro Phe Val Ala Ile Gln Ala Ala
        115                 120                 125

Gln Ala Ser Met Pro Asp Gly Gly Arg Ile Ile Asn Ile Gly Ser Cys
    130                 135                 140

Leu Ala Glu Arg Ala Gly Arg Ala Gly Val Thr Leu His Ala Ala Ser
145                 150                 155                 160

Lys Ser Ala Leu Leu Gly Met Thr Arg Gly Leu Ala Arg Asp Leu Gly
                165                 170                 175

Ala Arg Gly Ile Thr Ala Asn Val Val His Pro Gly Pro Ile Asp Thr
```

```
            180                 185                 190
Asp Met Asn Pro Ala Asp Gly Glu Arg Ser Gly Glu Leu Val Ala Val
            195                 200                 205

Leu Ser Leu Pro His Tyr Gly Glu Val Arg Asp Ile Ala Gly Met Val
        210                 215                 220

Ala Phe Leu Ala Gly Pro Asp Gly Arg Tyr Val Thr Gly Ala Ser Leu
225                 230                 235                 240

Ala Val Asp Gly Gly Phe Ala Ala
                245

<210> SEQ ID NO 5
<211> LENGTH: 248
<212> TYPE: PRT
<213> ORGANISM: Artificial Sequence
<220> FEATURE:
<223> OTHER INFORMATION: mBFP Y157N w/o his-tag

<400> SEQUENCE: 5

Met Gln Asn Leu Asn Gly Lys Val Ala Phe Val Thr Gly Gly Ser Arg
1               5                   10                  15

Gly Ile Gly Ala Ala Ile Val Arg Arg Leu Ala Ala Asp Gly Ala Asp
            20                  25                  30

Ile Ala Phe Thr Tyr Val Ser Ala Ser Ser Lys Asn Val Ala Thr Ala
        35                  40                  45

Leu Val Gln Glu Leu Glu Ala Lys Gly Arg Arg Ala Arg Ala Ile Gln
    50                  55                  60

Ala Asp Ser Ala Asp Pro Ala Gln Val Arg Gln Ala Val Glu Gln Ala
65                  70                  75                  80

Ile Val Gln Leu Gly Pro Val Asp Val Leu Val Asn Asn Ala Gly Ile
                85                  90                  95

Phe Leu Ala Gly Pro Leu Gly Glu Val Thr Leu Asp Asp Tyr Glu Arg
            100                 105                 110

Thr Met Asn Ile Asn Val Arg Ala Pro Phe Val Ala Ile Gln Ala Ala
        115                 120                 125

Gln Ala Ser Met Pro Asp Gly Gly Arg Ile Ile Asn Ile Gly Ser Cys
    130                 135                 140

Leu Ala Glu Arg Ala Gly Arg Ala Gly Val Thr Leu Asn Ala Ala Ser
145                 150                 155                 160

Lys Ser Ala Leu Leu Gly Met Thr Arg Gly Leu Ala Arg Asp Leu Gly
                165                 170                 175

Ala Arg Gly Ile Thr Ala Asn Val Val His Pro Gly Pro Ile Asp Thr
            180                 185                 190

Asp Met Asn Pro Ala Asp Gly Glu Arg Ser Gly Glu Leu Val Ala Val
        195                 200                 205

Leu Ser Leu Pro His Tyr Gly Glu Val Arg Asp Ile Ala Gly Met Val
    210                 215                 220

Ala Phe Leu Ala Gly Pro Asp Gly Arg Tyr Val Thr Gly Ala Ser Leu
225                 230                 235                 240

Ala Val Asp Gly Gly Phe Ala Ala
                245

<210> SEQ ID NO 6
<211> LENGTH: 248
<212> TYPE: PRT
<213> ORGANISM: Artificial Sequence
<220> FEATURE:
<223> OTHER INFORMATION: BFP wild type Y157 w/o his-tag
```

<400> SEQUENCE: 6

```
Met Gln Asn Leu Asn Gly Lys Val Ala Phe Val Thr Gly Gly Ser Arg
1               5                   10                  15

Gly Ile Gly Ala Ala Ile Val Arg Arg Leu Ala Ala Asp Gly Ala Asp
            20                  25                  30

Ile Ala Phe Thr Tyr Val Ser Ala Ser Ser Lys Asn Val Ala Thr Ala
        35                  40                  45

Leu Val Gln Glu Leu Glu Ala Lys Gly Arg Arg Ala Arg Ala Ile Gln
50                  55                  60

Ala Asp Ser Ala Asp Pro Ala Gln Val Arg Gln Ala Val Glu Gln Ala
65                  70                  75                  80

Ile Val Gln Leu Gly Pro Val Asp Val Leu Val Asn Asn Ala Gly Ile
                85                  90                  95

Phe Leu Ala Gly Pro Leu Gly Glu Val Thr Leu Asp Asp Tyr Glu Arg
            100                 105                 110

Thr Met Asn Ile Asn Val Arg Ala Pro Phe Val Ala Ile Gln Ala Ala
        115                 120                 125

Gln Ala Ser Met Pro Asp Gly Gly Arg Ile Ile Asn Ile Gly Ser Cys
130                 135                 140

Leu Ala Glu Arg Ala Gly Arg Ala Gly Val Thr Leu Tyr Ala Ala Ser
145                 150                 155                 160

Lys Ser Ala Leu Leu Gly Met Thr Arg Gly Leu Ala Arg Asp Leu Gly
                165                 170                 175

Ala Arg Gly Ile Thr Ala Asn Val Val His Pro Gly Pro Ile Asp Thr
            180                 185                 190

Asp Met Asn Pro Ala Asp Gly Glu Arg Ser Gly Glu Leu Val Ala Val
        195                 200                 205

Leu Ser Leu Pro His Tyr Gly Glu Val Arg Asp Ile Ala Gly Met Val
210                 215                 220

Ala Phe Leu Ala Gly Pro Asp Gly Arg Tyr Val Thr Gly Ala Ser Leu
225                 230                 235                 240

Ala Val Asp Gly Gly Phe Ala Ala
                245
```

<210> SEQ ID NO 7
<211> LENGTH: 32
<212> TYPE: DNA
<213> ORGANISM: Artificial Sequence
<220> FEATURE:
<223> OTHER INFORMATION: primer X-BFP F

<400> SEQUENCE: 7
aatctagaat gcagaatctg aacggcaaag tg         32

<210> SEQ ID NO 8
<211> LENGTH: 28
<212> TYPE: DNA
<213> ORGANISM: Artificial Sequence
<220> FEATURE:
<223> OTHER INFORMATION: primer X-BFP R

<400> SEQUENCE: 8
aagaattctt aagcggcgaa gccgccgt              28

<210> SEQ ID NO 9
<211> LENGTH: 33
<212> TYPE: DNA

```
<213> ORGANISM: Artificial Sequence
<220> FEATURE:
<223> OTHER INFORMATION: primer HcC-BFP F

<400> SEQUENCE: 9
atagaattca tgcagaatct gaacggcaaa gtg                              33

<210> SEQ ID NO 10
<211> LENGTH: 30
<212> TYPE: DNA
<213> ORGANISM: Artificial Sequence
<220> FEATURE:
<223> OTHER INFORMATION: primer Hc-BFP R

<400> SEQUENCE: 10
atagcggccg cttaagcggc gaagccgccg                                  30

<210> SEQ ID NO 11
<211> LENGTH: 28
<212> TYPE: DNA
<213> ORGANISM: Artificial Sequence
<220> FEATURE:
<223> OTHER INFORMATION: primer C-BFP R

<400> SEQUENCE: 11
aatctagatt aagcggcgaa gccgccgt                                    28
```